United States Patent

Moinet et al.

Patent Number: 6,143,787
Date of Patent: Nov. 7, 2000

[54] PHARMACEUTICAL COMPOSITION CONTAINING 4-OXO-BUTYNIC ACIDS

[75] Inventors: Gérard Moinet, Orsay; Liliane Doare, Viry-Chatillon; Micheline Kergoat, Bures sur Yvette; Philippe Maizeray, Vanves; Didier Mesangeau, Combs la Ville, all of France

[73] Assignee: Merck Patent Gesellschaft Mit, Germany

[21] Appl. No.: 09/230,849

[22] PCT Filed: Aug. 5, 1997

[86] PCT No.: PCT/EP97/04252

§ 371 Date: Feb. 2, 1999

§ 102(e) Date: Feb. 2, 1999

[87] PCT Pub. No.: WO98/07681

PCT Pub. Date: Feb. 26, 1998

[30] Foreign Application Priority Data

Aug. 16, 1996 [FR] France .................................. 96 10254

[51] Int. Cl.$^7$ ...................................................... A61K 31/19
[52] U.S. Cl. .......................... 514/568; 514/569; 514/464; 514/461; 562/459; 562/462; 549/436; 549/501
[58] Field of Search ...................................... 514/569, 568, 514/464, 401; 562/462, 459; 549/436, 501

[56] References Cited

U.S. PATENT DOCUMENTS 5,055,466 10/1991 Weller, III et al. .

FOREIGN PATENT DOCUMENTS 2623507 5/1989 France .

OTHER PUBLICATIONS

Galardy et al, Chemical Abstracts, vol. 100, No. 152956n, 1984.

*Primary Examiner*—James H. Reamer
*Attorney, Agent, or Firm*—Millen, White, Zelano & Branigan, P.C.

[57] ABSTRACT

The present invention relates to a pharmaceutical composition comprising, as active principle, a compound of formula:

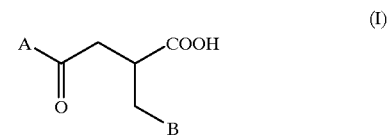

(I)

in which the groups A and B are chosen, independently of each other, from:
- a mono-, bi- or tricyclic aryl group having from 6 to 14 carbon atoms;
- a heteroaromatic group chosen from pyridyl, pyrimidyl, pyrrolyl, furyl and thienyl groups;
- an alkyl group having from 1 to 14 carbon atoms;
- a cycloalkyl group having from 5 to 8 carbon atoms;
- a saturated heterocyclic group chosen from tetrahydrofuryl, tetrahydropyranyl, piperidyl and pyrrolidinyl groups;

to its solvate or to a salt of this acid with a pharmaceutically acceptable base.

Figures: none.

14 Claims, No Drawings

PHARMACEUTICAL COMPOSITION CONTAINING 4-OXO-BUTYNIC ACIDS

The present invention relates to pharmaceutical compositions containing 4-oxobutanoic acids, which are useful in particular in the treatment of diabetes.

The subject of the present invention is thus pharmaceutical compositions comprising, as, active principle, a compound of formula:

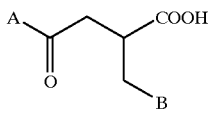

(I)

in which the groups A and B are chosen, independently of each other, from:
- a mono-, bi- or tricyclic aryl group having from 6 to 14 carbon atoms;
- a heteroaromatic group chosen from pyridyl, pyrimidyl, pyrrolyl, furyl and thienyl groups;
- an alkyl group having from 1 to 14 carbon atoms;
- a cycloalkyl group having from 5 to 8 carbon atoms;
- a saturated heterocyclic group chosen from tetrahydrofuryl, tetrahydropyranyl, piperidyl and pyrrolidinyl groups;
- it being possible for the groups A and B to bear 1 to 3 substituents chosen from a $C_1$–$C_6$ alkyl group, $C_1$–$C_6$ alkoxy group, $C_6$–$C_{14}$ aryl group, a heteroaryl group chosen from pyridyl, pyrimidyl, pyrrolyl, furyl and thienyl, a ($C_6$–$C_{14}$)aryl($C_1$–$C_6$)alkyl group, a ($C_6$–$C_{14}$)aryl($C_1$–$C_6$)alkyl($C_6$–$C_{14}$)aryl group, halogen, a trifluoromethyl, trifluoromethoxy, cyano, hydroxyl, nitro, amino, carboxyl, ($C_1$–$C_6$)alkoxycarbonyl, carbamoyl, ($C_1$–$C_6$) alkylsulphonyl, sulphoamino, ($C_1$–$C_6$)alkylsulphonylamino, sulphamoyl or ($C_1$–$C_6$) alkylcarbonylamino group,
- or two of the substituents forming a methylenedioxy group, its solvate or a salt of this acid with a pharmaceutically acceptable base.

In a preferred embodiment of the invention, the compositions comprise, as active principles, a compound of formula I in which A and B are chosen from aryl groups.

Examples of aryl groups which may be mentioned are phenyl, α-naphthyl, β-naphthyl and fluorenyl groups.

The $C_1$–$C_6$ alkyl groups may be linear or branched. Examples which may be mentioned are methyl, ethyl, propyl, isopropyl, butyl, isobutyl, tert-butyl and pentyl groups.

The $C_1$–$C_6$ alkoxy groups may similarly be linear or branched.

Examples which may be mentioned are methoxy, ethoxy, propoxy, isopropoxy, butoxy, and isobutoxy groups.

The halogens may be chosen from fluorine, chlorine, bromine and iodine.

The present invention encompasses compositions which contain the tautomeric forms, the enantiomers, the diastereoisomers and the epimers of the compounds of formula I.

Examples of pharmaceutically acceptable salts which may be mentioned are the sodium salts, potassium salts, magnesium salts, calcium salts, amine salts and other salts of the same type (aluminium, iron, bismuth, etc.).

In a preferred embodiment, the compositions according to the invention comprise a compound chosen from:

2-benzyl-4-(4-methoxyphenyl)-4-oxobutanoic acid
2-benzyl-4-(4-fluorophenyl)-4-oxobutanoic acid
2-cyclohexylmethyl-4-(4-methoxyphenyl)-4-oxobutanoic acid
2-benzyl-4-phenyl-4-oxobutanoic acid
2-(β-naphthylmethyl)-4-phenyl-4-oxobutanoic acid
2-benzyl-4-(β-naphthyl)-4-oxobutanoic acid
2-[(4-chlorophenyl)methyl]-4-(4-methoxyphenyl)-4-oxobutanoic acid
2-benzyl-4-(4-methylphenyl)-4-oxobutanoic acid
4-(4-fluorophenyl)-2-[(4-methoxyphenyl)methyl]-4-oxobutanoic acid
2-benzyl-4-(3,4-methylenedioxyphenyl)-4-oxobutanoic acid
2-benzyl-4-cyclohexyl-4-oxobutanoic acid
4-phenyl-2-[(2-tetrahydrofuryl)methyl]-4-oxobutanoic acid, the solvates and the salts of these acids with pharmaceutically acceptable bases.

Certain compounds of formula I are known (Bioorg. Chem. 14, 148, 1986; Biochemistry 23, 2083, 1984; J.A.C.S. 100, 7750, 1978; EP-A-310918 and DE-A-3 839 401)

The subject of the present invention is also the novel compounds of formula I, that is to say the compounds of formula:

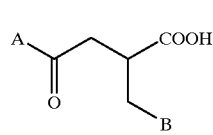

(I)

in which the groups A and B are chosen, independently of each other, from:
- a mono-, bi- or tricyclic aryl group having from 6 to 14 carbon atoms;
- a heteroaromatic group chosen from pyridyl, pyrimidyl, pyrrolyl, furyl and thienyl groups;
- an alkyl group having from 1 to 14 carbon atoms;
- a cycloalkyl group having from 5 to 8 carbon atoms;
- a saturated heterocyclic group chosen from tetrahydrofuryl, tetrahydropyrranyl, piperidyl and pyrrolidinyl groups;
- it being possible for the groups A and B to bear 1 to 3 substituents chosen from a $C_1$–$C_6$ alkyl group, $C_1$–$C_6$ alkoxy group, $C_6$–$C_{14}$ aryl group, a heteroaryl group chosen from pyridyl, pyrimidyl, pyrrolyl, furyl and thienyl, a ($C_6$–$C_{14}$)aryl($C_1$–$C_6$)alkyl group, a ($C_6$–$Cl_4$)aryl($C_1$–$C_6$)alkyl($C_6$–$C_{14}$)aryl group, halogen, a trifluoromethyl, trifluoromethoxy, cyano, hydroxyl, nitro, amino, carboxyl, ($C_1$–$C_6$) alkoxycarbonyl, carbamoyl, ($C_1$–$C_6$) alkylsulphonyl, sulphoamino, ($C_1$–$C_6$) alkylsulphonylamino, sulphamoyl or ($C_1$–$C_6$) alkylcarbonylamino group,
- or two of the substituents forming a methylenedioxy group,
- with the exclusion of the compounds of formula I in which B is an unsubstituted phenyl group and A is a phenyl, 4-methoxyphenyl, 4-chlorophenyl or cyclohexyl group,
- their solvates and the salts of these acids with bases.

The novel compounds include the salts of the acids with pharmaceutically acceptable bases or other bases which give salts which may serve to identify, purify or resolve the compounds of formula I.

The compounds of formula I may be prepared according to a malonic synthesis which consists in reacting a compound of formula:

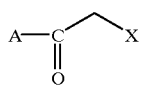

(II)

in which X is a halogen as defined above and A has the meaning given above, with a malonic derivative of formula:

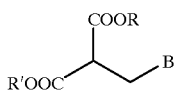

(III)

in which R and R' are $C_1$–$C_6$ alkyl groups and B has the meaning given above, in the presence of an alkali metal hydride or an alkali metal alkoxide, in order to form a compound of formula:

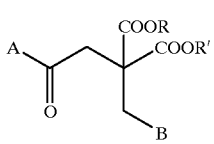

(IV)

in which A, B, R and R' have the meaning given above, and then in saponifying the compound of formula IV, for example with a mixture of alkaline hydroxide, water, tetrahydrofuran and/or ethanol, in order to form a compound of formula:

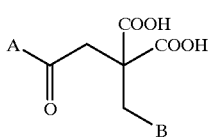

(V)

and then in decarboxylating the compound of formula V, in particular by heating to dryness, in order to give the compound of formula I.

The enantiomers of the compounds of formula (I) may be separated by successive recrystallization of the salt of the acid (I) with an optically active base in solvents such as acetone, ethyl acetate, isopropanol, etc., followed by displacement of the optically active acid from the salt by an inorganic or organic acid according to a standard method.

The compositions according to the present invention may be used in the treatment of diabetes, in particular insulin-independent diabetes, on account of their hypoglycaemiating effect and their absence of toxicity at active doses.

The pharmaceutical compositions according to the invention may be provided in forms intended for parenteral, oral, rectal, permucous or percutaneous administration.

They will thus be in the form of multi-dose bottles or injectable solutions or suspensions, in the form of plain or coated tablets, sugar-coated tablets, wafer capsules, gelatin capsules, pills, cachets, powders, suppositories, rectal capsules, solutions or suspensions, for percutaneous use in a polar solvent, or for permucous use.

The excipients which are suitable for such administrations are cellulose derivatives or microcrystalline cellulose, alkaline-earth metal carbonates, magnesium phosphate, starches, modified starches and lactose for solid forms.

For rectal use, cocoa butter or polyethylene glycol stearates are the preferred excipients.

For parenteral use, water, aqueous solutions, physiological saline and isotonic solutions are the vehicles most conveniently used.

The dosage may vary within a wide range depending on the therapeutic indication and the route of administration, as well as on the age and weight of the patient.

The examples which follow illustrate the preparation of the compounds of formula I.

EXAMPLE 1

Preparation of 2-benzyl-4-(4-methoxyphenyl)-4-oxobutanoic acid (product No. 2)

A—Preparation of diethyl 2-benzyl-2-[2-(4-methoxyphenyl)-2-oxoethyl]propanedioate A mixture of 24 ml of diethyl 2-benzylmalonate, 3 g of 80% sodium hydride in oil (washed beforehand with petroleum ether) and 150 ml of tetrahydrofuran is heated at 70° C. for 1 hour. 24 g of 2-bromo-4'-methoxyacetophenone dissolved in 50 ml of tetrahydrofuran are added, at +5° C., over 1 hour. After one night at room temperature, the reaction mixture is poured into 400 ml of water. After extraction with ethyl acetate, the organic solution is washed with brine, dried over magnesium sulphate and concentrated to dryness under reduced pressure. 40 g of a yellow oil which crystallizes are obtained.

m.p.=67° C. (hexane) I.R. (KBr): ν CO (ketone)=1671 $cm^{-1}$; ν CO (ester)=1735 $cm^{-1}$ $^1$H NMR (DMSO/TMS) 1.2 (6H, t, 2CH$_3$); 3.35 (4H, d, 2CH$_2$); 3.8 (3H, s, OCH$_3$); 4.1 (4H, q. 2OCH$_2$); 7.1 (7H, m, aromatic H); 7.85 (2H, d, aromatic H).

B—Preparation of 2-benzyl-2-[2-(4-methoxyphenyl)-2-oxoethyl]propanedioic acid 30 g of diethyl 2-benzyl-2-[2-(4-methoxyphenyl)-2-oxoethyl]propanedioate, 80 ml of aqueous 2N sodium hydroxide and 250 ml of tetrahydrofuran are mixed together with vigorous stirring.

After 5 days at room temperature, the reaction mixture is poured onto 1 litre of ice-water. The mixture is washed twice with 200 ml of ethyl acetate and is then acidified, while cold, with 60 ml of aqueous 3N hydrochloric acid.

The mixture is extracted with 3 times 200 ml of ethyl acetate. The organic phase is washed with 100 ml of neutral water, 100 ml of brine and then dried over magnesium sulphate and, finally, concentrated to dryness under reduced pressure. The greasy yellow solid is recrystallized from acetonitrile. 18 g of a white solid are obtained.

m.p.=175° C., decomp. I.R. (KBr): ν CO (ketone)=1660 $cm^{-1}$; ν CO (acid)=1749 $cm^{-1}$ $^1$H NMR (DMSO/TMS) 3.1 (4H, S, 2CH$_2$); 3.8 (3H, S, OCH$_3$); 7 (7H, m, aromatic H); 7.8 (2H, d, aromatic H); 13.7 (m, OH).

C—Preparation of 2-benzyl-4-(4-methoxyphenyl)-4-oxobutanoic acid 17 g of 2-benzyl-2-[2-(4-methoxyphenyl)-2-oxo-ethyl]propanedioic acid are heated with stirring until they melt. When the evolution of gas has ceased, the heating is stopped and the material is cooled to room temperature. The yellow solid is recrystallized from ethyl acetate. 12 g of a white solid are obtained.

m.p.=131° C. I.R. (KBr) ν CO (ketone)=1664 cm$^{-1}$; ν CO (acid)=1729 cm$^{-1}$ $^1$H NMR (DMSO/TMS) 3.1 (5H, m, CH and 2CH$_2$); 3.8 (3H, s, OCH$_3$); 7.1 (7H, m, aromatic H); 7.9 (2H, d, aromatic H); 13.5 (m, OH).

EXAMPLE 2

Preparation of (−)-2-benzyl-4-(4-methoxyphenyl)-4-oxobutanoic acid (product No. 3)

20 g of the acid obtained in Example 1 are dissolved in 200 ml of warm acetone. 8.12 g of S-(−)-α-methylbenzylamine dissolved in 40 ml of acetone are added. The mixture is cooled and the white solid is filtered off and drained. After successive recrystallization from isopropanol until the optical deviation of the salt is stable, 7.3 g of a salt are obtained, which product is treated with 100 ml of 2N hydrochloric acid and 50 ml of ethyl ether with vigorous stirring. The mixture is separated after settling has taken place and the acidic aqueous phase is extracted again with 50 ml of ethyl ether. The combined ether solutions are washed once with neutral water and then once with brine. The organic solution is then dried over magnesium sulphate and concentrated to dryness under reduced pressure at room temperature. The residual oil crystallizes from pentane. 5.1 g of a white solid are obtained.

m.p. =94° C. HPLC purity>95%; $[\alpha]^{22}_D$=−18° 1 (c=5, EtOAc).

EXAMPLE 3

Preparation of (+)-2-benzyl-4-(4-methoxyphenyl)-4-oxobutanoic acid (product No. 4)

The technique is the same as that used to separate the (−) acid, except that R-(+)-α-methylbenzylamine is used here. A white solid is obtained.

m.p.=93° C.; HPLC=98%; $[\alpha]^{19}_D$=+17° 6 (c=5, EtOAc).

EXAMPLE 4

Preparation of 2-benzyl-4-(4-fluorophenyl)-4-oxobutanoic acid (product No. 5)
A—Preparation of ethyl 2-benzyl-2-[2-(4-fluorophenyl)-2-oxoethyl]propanedioate The process is performed in the same way as in Example 1, stage A. A copper-yellow oil is obtained.

I.R. (film): ν CO (ketone)=1687 cm$^{-1}$; ν CO (ester)=1735 cm$^{-1}$.

$^1$H NMR (DMSO/TMS)=1.25 (6H, t, 2CH$_3$); 3.5 (4H, d, 2CH$_2$); 4.2 (4H, q. 2OCH$_2$); 6.8–8 (9H, m, aromatic H).

B—Preparation of 2-benzyl-2-[2-(4-fluorophenyl)-2-oxoethyl]propanedioic acid

The process is performed in the same way as in Example 1, stage B. A white solid is obtained. m.p.=185–90° C. (acetonitrile)

I.R. (KBr): ν CO (ketone)=1675 cm$^{-1}$; ν CO (acid)=1747 cm$^{-1}$.

$^1$H NMR (DMSO/TMS): 3.3 (4H, d, 2CH$_2$); 6.7-8 (9H, m, aromatic H); 13 (m, OH).

C—Preparation of 2-benzyl-4-(4-fluorophenyl)-4-oxobutanoic acid

The process is performed in the same way as in Example 1, stage C. A yellow solid is obtained, which is recrystallized from acetonitrile. The white solid thus obtained corresponds to the acid.

m.p.=140° C.

I.R. (KBr): ν CO (ketone)=1683 cm$^{-1}$; ν CO (acid)=1708 cm$^{-1}$.

$^1$H NMR (DMSO/TMS): 3 (5H, m, CH and 2CH$_2$); 7–8.1 (9H, m, aromatic H); 12.2 (s, OH).

EXAMPLE 5

Preparation of (+)-2-benzyl-4-(4-fluorophenyl)-4-oxobutanoic acid (product No. 6)

The same method is used as in Example 4. A white solid is obtained.

m.p.=88° C.; HPLC=99.8%; $[\alpha]^{22}_D$=+9°9 (c=5, EtOAc)

EXAMPLE 6

Preparation of (−)-2-benzyl-4-(4-fluorophenyl)-4-oxobutanoic acid (product No. 7)

The same method as in Example 3 is used. A white solid is obtained.

m.p.=89° C.; HPLC=98.5%; $[\alpha]^{22}_D$=−8°9 (c=10, EtAOc).

The characteristics of the compounds of formula I are collated in Table I below.

TABLE I

| Product No. | STRUCTURE | m.p. in ° C. (Köfler) | Calculated C H | Found C H |
|---|---|---|---|---|
| 1 | 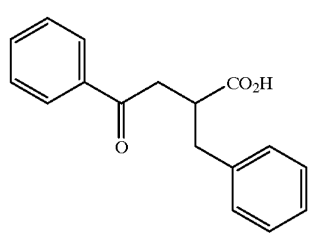 | 173 | 76.10 6.01 | 75.96 5.93 |

TABLE I-continued

| Product No. | STRUCTURE | m.p. in °C. (Köfler) | Calculated C H | Found C H | |
|---|---|---|---|---|---|
| 2 | 4-MeO-C6H4-CO-CH2-CH(CO2H)-CH2-C6H5 | 131 | 72.47 6.08 | 72.36 6.13 | |
| 3 | 4-MeO-C6H4-CO-CH2-CH(CO2H)-CH2-C6H5 (−) | 94 | 72.47 6.06 | 72.42 6.15 | $[\alpha]_D^{22}$ α − 18° 1 (c = 5, EtOAc) |
| 4 | 4-MeO-C6H4-CO-CH2-CH(CO2H)-CH2-C6H5 (+) | 93 | 72.47 6.08 | 72.35 6.11 | $[\alpha]_D^{19}$ α + 17° 6 (c = 5, EtOAc) |
| 5 | 4-F-C6H4-CO-CH2-CH(CO2H)-CH2-C6H5 | 140 | 71.32 5.28 | 71.30 5.33 | |
| 6 | 4-F-C6H4-CO-CH2-CH(CO2H)-CH2-C6H5 (−) | 88 | 71.32 5.28 | 71.18 5.24 | $[\alpha]_D^{22}$ α + 9° 9 (c = 5, EtOAc) |
| 7 | 4-F-C6H4-CO-CH2-CH(CO2H)-CH2-C6H5 (−) | 89 | 71.32 5.28 | 71.37 5.35 | $[\alpha]_D^{20}$ α − 8° 9 (c = 10, EtOAc) |

TABLE I-continued

| Product No. | STRUCTURE | m.p. in °C. (Köfler) | Calculated C H | Found C H |
|---|---|---|---|---|
| 8 | (phenyl-C(O)-CH2-CH(CO2H)-CH2-2-naphthyl) | 118 | 79.22 5.70 | 79.11 5.82 |
| 9 | (2-naphthyl-C(O)-CH2-CH(CO2H)-CH2-phenyl) | 139 | 79.22 5.70 | 79.21 5.73 |
| 10 | (4-MeO-C6H4-C(O)-CH2-CH(CO2H)-CH2-4-Cl-C6H4) | 157 | 64.97 5.15 | 64.90 5.19 |
| 11 | (4-MeO-C6H4-C(O)-CH2-CH(CO2H)-CH2-cyclohexyl) | 129 | 71.03 7.95 | 70.90 7.93 |
| 12 | (4-Me-C6H4-C(O)-CH2-CH(CO2H)-CH2-phenyl) | 129 | 76.57 6.43 | 76.57 6.53 |
| 13 | (4-F-C6H4-C(O)-CH2-CH(CO2H)-CH2-4-OMe-C6H4) | 96 | 68.35 5.42 | 68.33 5.55 |

TABLE I-continued

| Product No. | STRUCTURE | m.p. in °C. (Köfler) | Calculated C H | Found C H |
|---|---|---|---|---|
| 14 | benzodioxole-C(O)-CH$_2$-CH(CO$_2$H)-CH$_2$-phenyl | 161–2 | 69.22 5.16 | 69.21 5.19 |
| 15 | cyclohexyl-C(O)-CH$_2$-CH(CO$_2$H)-CH$_2$-phenyl | 74 | 74.42 8.06 | 74.35 8.16 |
| 16 | phenyl-C(O)-CH$_2$-CH(CO$_2$H)-CH$_2$-(tetrahydrofuran-2-yl) | 88 | 68.68 6.92 | 68.55 6.95 |

Results of the pharmacological studies will be given below.

1—Study of the Antidiabetic Activity in nOSTZ Rats

The antidiabetic activity of the compounds of formula I was determined orally on an experimental model of insulin-independent diabetes induced in rats by streptozocin.

The model of insulin-independent diabetes is obtained in rats by neonatal injection (on the day of birth) of streptozocin.

The diabetic rats used are 8 weeks old.

Stabling of the animals is carried out, from the day of their birth to the day of the experiment, in an animal house at a controlled temperature of 21 to 22° C., and subjected to a fixed cycle of light (from 7.00 h to 19.00 h) and of darkness (from 19.00 h to 7.00 h). Their feeding consisted of a maintenance diet; water and food were supplied "ad libitum", with the exception of the 2-hour fasting period preceding the tests, during which the food is removed (postabsorptive state).

The rats are treated orally during the day with the test product. 2 hours after the final administration of the product and 30 minutes after anaesthetizing the animals with pentobarbital sodium (Nembutal®), a 300 µl blood sample is taken from the end of the tail.

Table II collates the main results obtained.

These results show the efficacy of the compounds of formula I for decreasing glycaemia in the diabetic animals.

Certain compounds of formula I also have a precocious insulin-secretory effect of short duration.

TABLE II

| Product No. | STRUCTURE | Glycaemia (%) 200 mg/Kg | Glycaemia (%) 20 mg/Kg | Insulinaemia (%) 200 mg/Kg | Insulinaemia (%) 20 mg/Kg |
|---|---|---|---|---|---|
| 1 | phenyl-C(O)-CH$_2$-CH(CO$_2$H)-CH$_2$-phenyl | −9 | −19 | 10 | −23 |

TABLE II-continued

| Product No. | STRUCTURE | Glycaemia (%) | | Insulinaemia (%) | |
|---|---|---|---|---|---|
| | | 200 mg/Kg | 20 mg/Kg | 200 mg/Kg | 20 mg/Kg |
| 2 | H₃CO-C₆H₄-CO-CH₂-CH(CH₂Ph)-CO₂H | −15 | −17 | 11 | −28 |
| 3 | H₃CO-C₆H₄-CO-CH₂-CH(CH₂Ph)-CO₂H (−) | (100) −33 | −8 | (100) −27 | −23 |
| 4 | H₃CO-C₆H₄-CO-CH₂-CH(CH₂Ph)-CO₂H (+) | (100) −37 | −22 | (100) −25 | −21 |
| 5 | F-C₆H₄-CO-CH₂-CH(CH₂Ph)-CO₂H | −39 | −22 | −25 | −42 |
| 6 | F-C₆H₄-CO-CH₂-CH(CH₂Ph)-CO₂H (+) | −30 | −16 | −33 | −17 |
| 7 | F-C₆H₄-CO-CH₂-CH(CH₂Ph)-CO₂H (−) | −37 | −14 | −7 | −33 |

TABLE II-continued
| Product No. | STRUCTURE | Glycaemia (%) | | Insulinaemia (%) | |
|---|---|---|---|---|---|
| | | 200 mg/Kg | 20 mg/Kg | 200 mg/Kg | 20 mg/Kg |
| 8 | 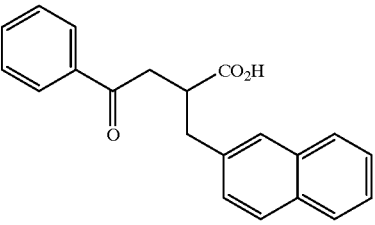 | −21 | −13 | −20 | 36 |
| 9 | 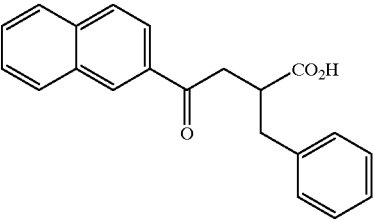 | −29 | −19 | 7 | 13 |
| 10 | 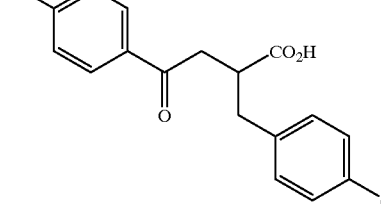 | −25 | −20 | −25 | −18 |
| 11 | 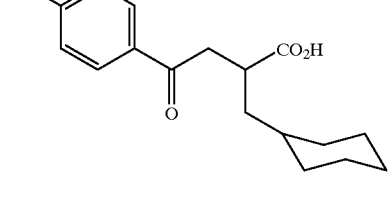 | −30 | −8 | 8 | 6 |
| 12 | 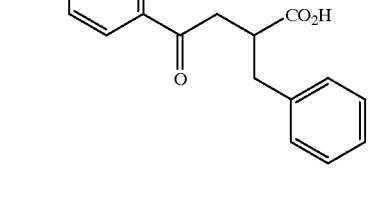 | −16 | −12 | −7 | 12 |
| 13 | 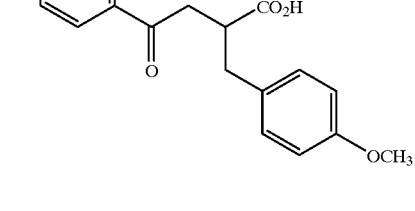 | −18 | 13 | −38 | 84 |

TABLE II-continued

| Product No. | STRUCTURE | Glycaemia (%) 200 mg/Kg | Glycaemia (%) 20 mg/Kg | Insulinaemia (%) 200 mg/Kg | Insulinaemia (%) 20 mg/Kg |
|---|---|---|---|---|---|
| 14 | 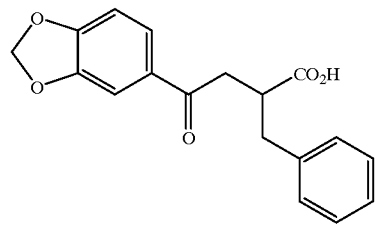 | −11 | −9 | 6 | 25 |
| 15 | 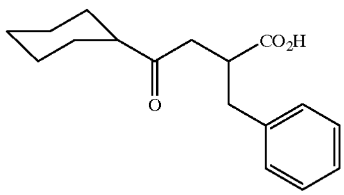 | −14 | −13 | −41 | 2 |
| 16 | 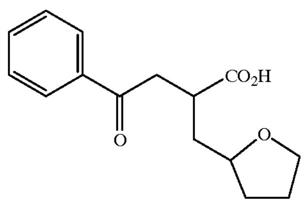 | −22 | −15 | −37 | 2 |

2—Study in Non-diabetic Rats

On the day of the experiment, non-diabetic rats are treated orally with the test product. 300 μl blood samples are taken from the end of the rats' tails in the first 30 minutes following administration of the product.

By way of example, the results obtained with product No. 5 (200 mg/kg p.o.) will be given.

TABLE III

| | Time after administration (min) | | | | |
|---|---|---|---|---|---|
| | 5 | 10 | 15 | 20 | 30 |
| % glycaemia | −4 | −11 | −25 | −31 | −35 |
| % insulinaemia | 102 | 94 | 57 | 55 | 52 |

A reduction in the glycaemia is observed, without observing any significant increase in the level of insulin, but rather a decrease in this level.

3—Test of Toxicity

Products Nos. 5 and 6 administered orally at a dose of 200 mg/kg induced no sign of toxicity.

4—Action on the Secretion of Glucagon

Experiments carried out in vitro on infused pancreas from non-diabetic rats, isolated according to the technique of Sussman et al., (*Diabetes* 15: 466, 1966) modified by Assan et al., (*Nature* 239: 125, 1972) showed that in the absence of glucose, in the infusion medium, as well as in the presence of arginine, the secretion of glucagon was stimulated by the compounds of formula I. Under the same conditions, sulphonylureas have a pronounced inhibitory effect. Nevertheless, in the presence of a high glucose concentration, the compounds of formula I do not modify the inhibition of the secretion of glucagon by glucose. The risks of hypoglycaemia associated with the treatment with sulphonylureas will thus be avoided during treatments with the compounds of formula I.

What is claimed is:

1. A pharmaceutical composition comprising a compound of formula:

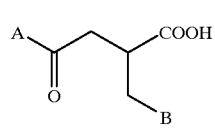

(I)

wherein A and B are chosen, independently of each other, from:

a mono-, bi- or tricyclic aryl group having from 6 to 14 carbon atoms;

a heteroaromatic group chosen from pyridyl, pyrimidyl, pyrrolyl, furyl and thienyl groups;

an alkyl group having from 1 to 14 carbon atoms;

a cycloalkyl group having from 5 to 8 carbon atoms; and a saturated heterocyclic group chosen from tetrahydrofuryl, tetrahydropyranyl, piperidyl and pyrrolidinyl groups;

wherein A and B are optionally substituted with 1 to 3 substituents chosen from a $C_1$–$C_6$ alkyl group, $C_1$–$C_6$ alkoxy group, $C_6$–$C_{14}$ aryl group, a heteroaryl group chosen from pyridyl, pyrimidyl, pyrrolyl, furyl and thienyl, a ($C_6$–$C_{14}$)aryl ($C_1$–$C_6$)alkyl group, a ($C_6$–$C_{14}$)

aryl ($C_1$–$C_6$)alkyl ($C_6$–$C_{14}$)aryl group, halogen, a trifluoromethyl, trifluoromethoxy, cyano, hydroxyl, nitro, amino, carboxyl, ($C_1$–$C_6$)alkoxycarbonyl, carbamoyl, ($C_1$–$C_6$)alkylsulphonyl, sulphoamino, ($C_1$–$C_6$)alkylsulphonylamino, sulphamoyl or ($C_1$–$C_6$) alkylcarbonylamino group, or two of the substituents form a methylenedioxy group, or a solvate or a salt thereof, and a pharmaceutically acceptable carrier.

2. A pharmaceutical composition according to claim 1, wherein A and B are, independently, a mono-, bi- or tricyclic aryl group having from 6 to 14 carbon atoms.

3. A pharmaceutical composition according to claim 1, wherein the compound of formula (I) is:

2-benzyl-4-(4-methoxyphenyl)-4-oxobutanoic acid 2-benzyl-4-(4-fluorophenyl)-4-oxobutanoic acid 2-cyclohexylmethyl-4-(4-methoxyphenyl)-4-oxobutanoic acid 2-benzyl-4-phenyl-4-oxobutanoic acid 2-(β-naphthylmethyl)-4-phenyl-4-oxobutanoic acid 2-benzyl-4-(β-naphthyl)-4-oxobutanoic acid 2-[(4-chlorophenyl)methyl]-4-(4-methoxyphenyl)-4-oxobutanoic acid 2-benzyl-4-(4-methylphenyl)-4-oxobutanoic acid 4-(4-fluorophenyl)-2—[(4-methoxyphenyl)methyl]-4-oxobutanoic acid 2-benzyl-4-(3,4-methylenedioxyphenyl)-4-oxobutanoic acid 2-benzyl-4-cyclohexyl-4-oxobutanoic acid 4-phenyl-2-[(2-tetrahydrofuryl)methyl]-4-oxobutanoic acid, or a solvate or salt thereof.

4. A compound of formula:

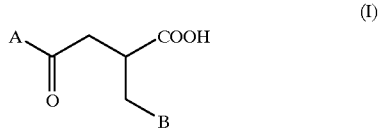

(I)

wherein A and B are chosen, independently of each other, from:

a mono-, bi- or tricyclic aryl group having from 6 to 14 carbon atoms;

a heteroaromatic group chosen from pyridyl, pyrimidyl, pyrrolyl, furyl and thienyl groups;

an alkyl group having from 1 to 14 carbon atoms;

a cycloalkyl group having from 5 to 8 carbon atoms; and a saturated heterocyclic group chosen from tetrahydrofuryl, tetrahydropyranyl, piperidyl and pyrrolidinyl groups;

wherein A and B are optionally substituted with 1 to 3 substituents chosen from a $C_1$–$C_6$ alkyl group, $C_1$–$C_6$ alkoxy group, $C_6$–$C_{14}$ aryl group, a heteroaryl group chosen from pyridyl, pyrimidyl, pyrrolyl, furyl and thienyl, a ($C_6$–$C_{14}$)aryl ($C_1$–$C_6$)alkyl group, a ($C_6$–$C_{14}$) aryl ($C_1$–$C_6$)alkyl ($C_6$–$C_{14}$)aryl group, halogen, a trifluoromethyl, trifluoromethoxy, cyano, hydroxyl, nitro, amino, carboxyl, ($C_1$–$C_6$)alkoxycarbonyl, carbamoyl, ($C_1$–$C_6$)alkylsulphonyl, sulphoaamino, ($C_1$–$C_6$)alkylsulphonylamino, sulphamoyl or ($C_1$–$C_6$) alkylcarbonylamino group, or two of the substituents form a methylenedioxy group, with the exclusion of compounds of formula I in which B is an unsubstituted phenyl group and A is a phenyl, 4-methoxyphenyl, 4-chlorophenyl or cyclohexyl group, or a solvate or salt thereof.

5. A pharmaceutical composition of claim 1, wherein the aryls of A and/or B are phenyl, α-naphthyl, β-naphthyl, or fluorenyl.

6. A pharmaceutical composition of claim 2, wherein the aryls of A and/or B are phenyl, α-naphthyl, β-naphthyl, or fluorenyl.

7. A pharmaceutical composition of claim 1, wherein the $C_1$–$C_6$ alkyl group which can substitute A and/or B is methyl, ethyl, propyl, isopropyl, butyl, isobutyl, tert-butyl or pentyl.

8. A pharmaceutical composition of claim 1, wherein the $C_1$–$C_6$ alkoxy group which can substitute A and/or B is methoxy, ethyoxy, propyoxy, isopropoxy, butyoxy, or isobutoxy.

9. A pharmaceutical composition of claim 1, wherein the halogen which can substitute A and/or B is fluorine, chlorine, bromine or iodine.

10. A pharmaceutical composition of claim 1, wherein the compound of formula (I) is in the form of a separated enantiomer.

11. A pharmaceutical composition of claim 1, wherein the compound of formula (I) is in the form of a diastereomer.

12. A method for treating diabetes, comprising administering to a patient in need of such treatment an effective amount of a pharmaceutical composition of claim 1.

13. The method of claim 12, wherein the diabetes is insulin-dependent diabetes.

14. The method of claim 12, wherein the pharmaceutical composition is administered by parenteral, oral, rectal, permucous or percutaneous administration.

* * * * *